United States Patent
Dinsmoor et al.

(10) Patent No.: US 9,585,642 B2
(45) Date of Patent: Mar. 7, 2017

(54) MINIMALLY INVASIVE IMPLANTABLE NEUROSTIMULATION SYSTEM

(71) Applicant: Medtronic, Inc., Minneapolis, MN (US)

(72) Inventors: David A. Dinsmoor, St. Paul, MN (US); Joel A. Anderson, Brooklyn Park, MN (US); Forrest C. M. Pape, New Brighton, MN (US); Todd V. Smith, Shoreview, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 418 days.

(21) Appl. No.: 14/098,728

(22) Filed: Dec. 6, 2013

(65) Prior Publication Data

US 2014/0163645 A1 Jun. 12, 2014

Related U.S. Application Data

(60) Provisional application No. 61/734,429, filed on Dec. 7, 2012, provisional application No. 61/777,949, filed on
(Continued)

(51) Int. Cl.
*A61N 1/378* (2006.01)
*A61N 1/36* (2006.01)
(Continued)

(52) U.S. Cl.
CPC .......... *A61B 17/00234* (2013.01); *A61N 1/02* (2013.01); *A61N 1/05* (2013.01);
(Continued)

(58) Field of Classification Search
CPC .. A61N 1/36139; A61N 1/05; A61N 1/37247; A61N 1/37252; A61N 1/36057;
(Continued)

(56) References Cited

U.S. PATENT DOCUMENTS 3,971,388 A 7/1976 Cowdery
6,051,017 A 4/2000 Loeb et al.
(Continued)

FOREIGN PATENT DOCUMENTS

CN 101522256 A 9/2009
CN 101522260 A 9/2009
(Continued)

OTHER PUBLICATIONS

U.S. Appl. No. 14/098,608, filed Dec. 6, 2013, by Tischendorf et al.
(Continued)

*Primary Examiner* — Mark W Bockelman
(74) *Attorney, Agent, or Firm* — Shumaker & Sieffert, P.A.

(57) ABSTRACT

Various embodiments of a minimally invasive implantable medical device (IMD) system are described. In one embodiment, the implantable medical device system includes an external device for transmitting a communication signal and an implantable device for receiving the communication signal by inductive coupling. The implantable device is configured to harvest power from the inductively coupled communication signal and power a signal generator from the harvested power to generate a therapeutic electrical stimulation signal.

25 Claims, 10 Drawing Sheets

Related U.S. Application Data on Mar. 12, 2013, provisional application No. 61/734,425, filed on Dec. 7, 2012, provisional application No. 61/777,804, filed on Mar. 12, 2013, provisional application No. 61/734,446, filed on Dec. 7, 2012, provisional application No. 61/777,824, filed on Mar. 12, 2013, provisional application No. 61/777,838, filed on Mar. 12, 2013, provisional application No. 61/734,436, filed on Dec. 7, 2012, provisional application No. 61/777,787, filed on Mar. 12, 2013.

(51) Int. Cl.

| | | |
|---|---|---|
| *A61N 1/372* | (2006.01) | |
| *A61B 17/00* | (2006.01) | |
| *A61N 1/05* | (2006.01) | |
| *A61N 1/02* | (2006.01) | |
| *A61N 1/375* | (2006.01) | |

(52) U.S. Cl.
CPC ............ *A61N 1/0551* (2013.01); *A61N 1/36* (2013.01); *A61N 1/3605* (2013.01); *A61N 1/36057* (2013.01); *A61N 1/36139* (2013.01); *A61N 1/3727* (2013.01); *A61N 1/3754* (2013.01); *A61N 1/3787* (2013.01); *A61N 1/37205* (2013.01); *A61N 1/37235* (2013.01); *A61N 1/37247* (2013.01); *A61N 1/37252* (2013.01); *A61N 1/36007* (2013.01); *A61N 1/36021* (2013.01); *A61N 1/36053* (2013.01); *A61N 1/36067* (2013.01); *A61N 1/36071* (2013.01); *A61N 1/375* (2013.01); *A61N 1/3756* (2013.01); *A61N 1/37211* (2013.01); *A61N 1/37223* (2013.01); *F04C 2270/0421* (2013.01)

(58) Field of Classification Search
CPC .. A61N 1/3787; A61N 1/3727; A61N 1/3754; A61N 1/02; A61N 1/0551; A61N 1/36; A61N 1/3605; A61N 1/37235; A61N 1/37205; A61N 1/375; A61N 1/3756; A61N 1/36007; A61N 1/36021; A61N 1/36053; A61N 1/36067; A61N 1/36071; A61N 1/37211; A61N 1/37223; A61B 17/00234

See application file for complete search history.

(56) References Cited

U.S. PATENT DOCUMENTS

| | | | |
|---|---|---|---|
| 6,975,906 | B2 | 12/2005 | Rusin et al. |
| 7,103,415 | B2 | 9/2006 | Probst et al. |
| 7,444,184 | B2 | 10/2008 | Boveja et al. |
| 7,467,014 | B2 | 12/2008 | Fuller et al. |
| 7,496,404 | B2 | 2/2009 | Meadows et al. |
| 7,860,570 | B2 | 12/2010 | Whitehurst et al. |
| 7,949,395 | B2 | 5/2011 | Kuzma |
| 8,989,861 | B2 | 3/2015 | Su et al. |
| 2003/0114905 | A1 | 6/2003 | Kuzma |
| 2005/0021119 | A1 | 1/2005 | Sage et al. |
| 2005/0092507 | A1 | 5/2005 | Marshall et al. |
| 2006/0085041 | A1 | 4/2006 | Hastings et al. |
| 2007/0123923 | A1 | 5/2007 | Lindstrom et al. |
| 2007/0156204 | A1 | 7/2007 | Denker et al. |
| 2008/0058871 | A1 | 3/2008 | Libbus et al. |
| 2008/0086181 | A1 | 4/2008 | Amurthur et al. |
| 2009/0118778 | A1 | 5/2009 | Biggs, Jr. et al. |
| 2009/0149900 | A1 | 6/2009 | Moffitt et al. |
| 2009/0157147 | A1 | 6/2009 | Cauller et al. |
| 2010/0023102 | A1 | 1/2010 | Spruit |
| 2010/0106223 | A1 | 4/2010 | Grevious et al. |
| 2010/0152808 | A1 | 6/2010 | Boggs, II |
| 2011/0301670 | A1 | 12/2011 | Gross et al. |
| 2012/0130398 | A1 | 5/2012 | Ackermann et al. |
| 2012/0303105 | A1 | 11/2012 | Askarinya et al. |

FOREIGN PATENT DOCUMENTS

| | | |
|---|---|---|
| CN | 101528303 A | 9/2009 |
| WO | 2004002572 A1 | 1/2004 |
| WO | 2009134466 A1 | 11/2009 |
| WO | 2010059096 A1 | 5/2010 |

OTHER PUBLICATIONS

U.S. Appl. No. 14/098,621, filed Dec. 6, 2013, by Tischendorf et al.
U.S. Appl. No. 14/099,462, filed Dec. 6, 2013, by Tischendorf et al.
U.S. Appl. No. 14/098,672, filed Dec. 6, 2013, by Scott et al.
International Search Report and Written Opinion from counterpart International Application No. PCT/US2013/073481, dated Feb. 10, 2014, 13 pages.
International Preliminary Report on Patentability from International Application No. PCT/US2013/073481, dated Jun. 18, 2015, 9 pp.

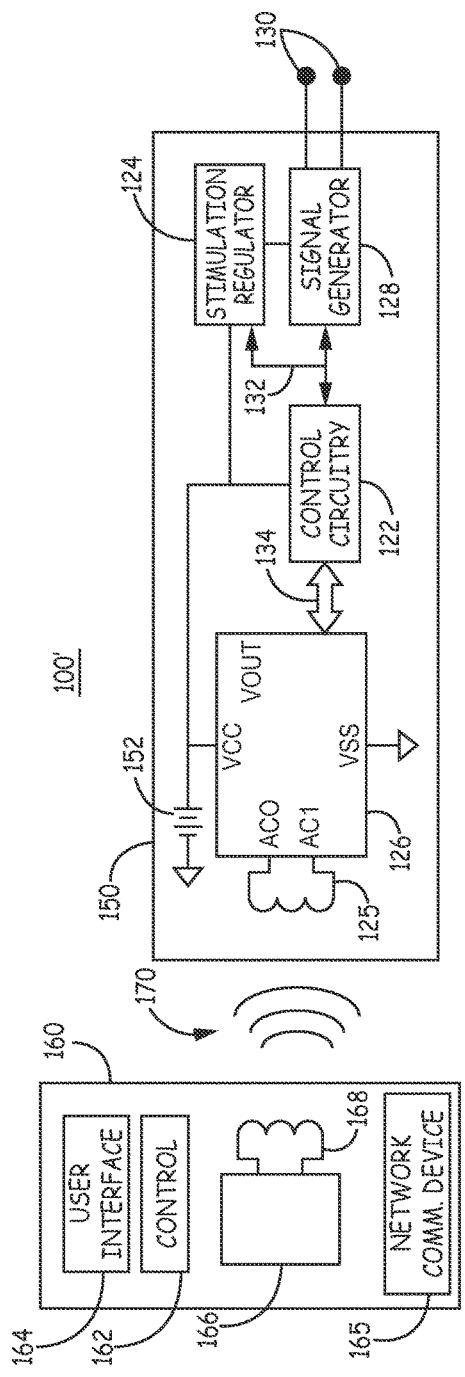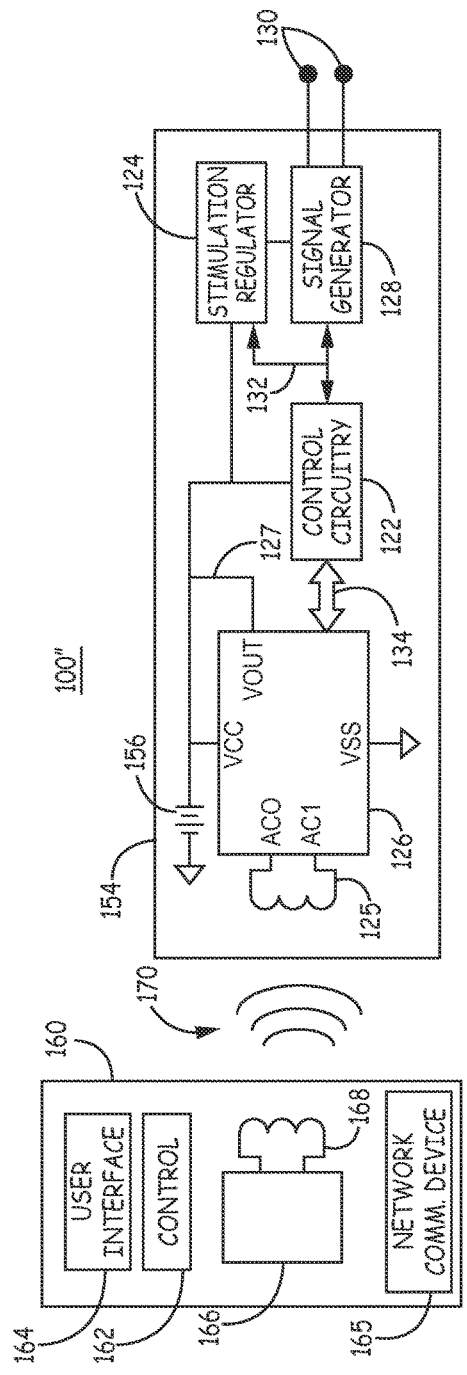
FIG. 4A
FIG. 4B

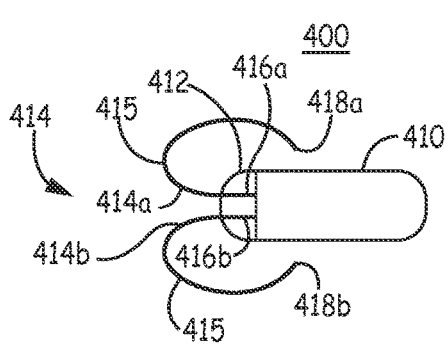
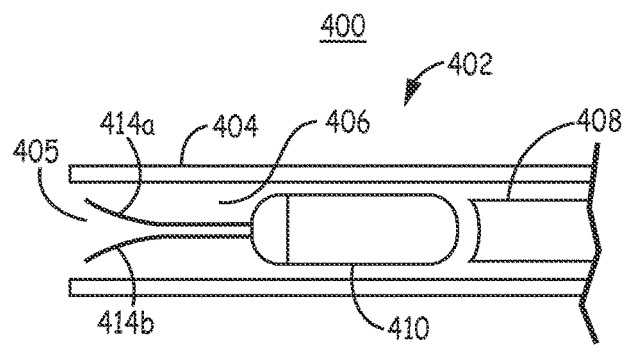
FIG. 8A    FIG. 8B
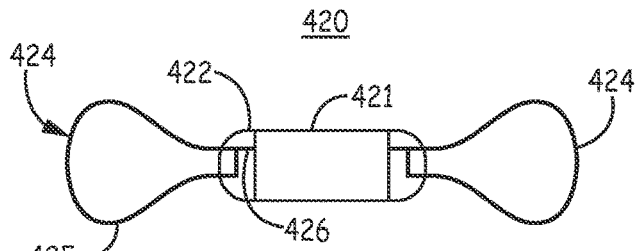
FIG. 9
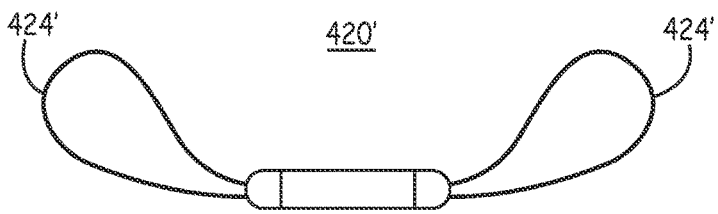
FIG. 10
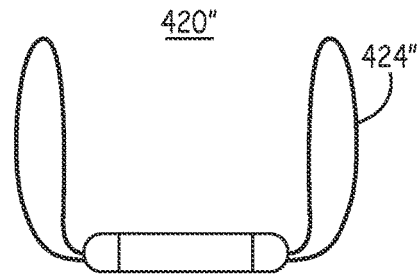
FIG. 11

MINIMALLY INVASIVE IMPLANTABLE NEUROSTIMULATION SYSTEM

CROSS-REFERENCE TO RELATED APPLICATIONS

The present application claims priority to U.S. Provisional Patent Application No. 61/734,425, filed Dec. 7, 2012, which application is incorporated herein by reference as if re-written in its entirety.

The present application claims priority to U.S. Provisional Patent Application No. 61/777,804, filed Mar. 12, 2013, which application is incorporated herein by reference as if re-written in its entirety.

The present application claims priority to U.S. Provisional Patent Application No. 61/734,429, filed Dec. 7, 2012, which application is incorporated herein by reference as if re-written in its entirety.

The present application claims priority to U.S. Provisional Patent Application No. 61/777,949, filed Mar. 12, 2013, which application is incorporated herein by reference as if re-written in its entirety.

The present application claims priority to U.S. Provisional Patent Application No. 61/734,446, filed Dec. 7, 2012, which application is incorporated herein by reference as if re-written in its entirety.

The present application claims priority to U.S. Provisional Patent Application No. 61/777,824, filed Mar. 12, 2013, which application is incorporated herein by reference as if re-written in its entirety.

The present application claims priority to U.S. Provisional Patent Application No. 61/777,838, filed Mar. 12, 2013, which application is incorporated herein by reference as if re-written in its entirety.

The present application claims priority to U.S. Provisional Patent Application No. 61/734,436, filed Dec. 7, 2012, which application is incorporated herein by reference as if re-written in its entirety.

The present application claims priority to U.S. Provisional Patent Application No. 61/777,787, filed Mar. 12, 2013, which application is incorporated herein by reference as if re-written in its entirety.

FIELD OF THE DISCLOSURE

The disclosure relates generally to implantable neurostimulation systems and in particular to minimally invasive implantable neurostimulation systems.

SUMMARY

Various exemplary embodiments of a minimally invasive implantable medical device (IMD) system are described. The exemplary IMD system includes an IMD configured for inductive communication with an external device, which may include power harvesting of a communication signal for powering at least some IMD functions. An exemplary IMD antenna is configured for receiving and transmitting communication signals and for providing fixation of the IMD at a target implant site in some embodiments.

In one embodiment, the IMD system includes an external device for transmitting a communication signal and an implantable device for receiving the communication signal by inductive coupling. The implantable device is configured to harvest power from the communication signal and provide a power signal to a signal generator from the harvested power to generate a therapeutic electrical stimulation signal.

The external medical device includes an inductive communication initiating device coupled to an external antenna. The implantable medical device includes a control unit, a signal generator for generating a therapeutic electrical stimulation signal, electrodes coupled to the signal generator for delivering the electrical stimulation signal to a neurostimulation site of a patient, an inductive communication target device coupled to an implantable antenna coupled for receiving the communication signal inductively coupled between the external antenna and the implantable antenna. The IMD further includes a rectifier coupled to the implantable antenna for receiving the inductively coupled communication signal and having a voltage output providing a voltage output signal in response to receiving the inductively coupled communication signal. The voltage output may be coupled to the signal generator to provide the voltage output signal to the signal generator for generating the therapeutic electrical stimulation signal delivered by the plurality of electrodes.

The voltage output of the rectifier may be the sole power source to the signal generator for generating the therapeutic electrical stimulation signal. The voltage output may be additionally coupled to the control unit and/or the target device to provide the voltage output signal to power at least one of the control unit and the target device. In some embodiments, the voltage output signal is the sole signal for powering functions of the implantable medical device. The rectifier generating the voltage output signal may include a rectifier included in the target device. The rectifier may include a rectifier coupled to the implantable antenna in parallel to the target device. In some embodiments, the implantable device includes a rechargeable energy storage device, and the voltage output is coupled to the rechargeable energy storage device for recharging the energy storage device.

The communication signal includes a carrier signal, and the external medical device may be enabled to apply the carrier signal to the external antenna for inductively coupling the carrier signal between the external antenna and the implantable antenna for generating the voltage output signal for a full duration of a neurostimulation therapy session. The external medical device may transmit the communication signal including an interval of communication data during the therapy session. The rectifier receives the inductively coupled signal during the interval of communication data and provides the voltage output signal in response to the inductively coupled signal.

The implantable medical device may be configured to start generating and delivering the electrical stimulation signal in response to receiving the communication signal from the external device upon the external device being within a communication range of the implantable medical device. The implantable medical device may include a sampling circuit coupled to the control unit and to a signal line for measuring a voltage signal correlated to the inductively coupled signal or the voltage output signal for providing the control unit with a feedback control signal. The implantable antenna may extend from the implantable medical device as a fixation member for stabilizing an implant position of the implantable medical device in some embodiments.

In one embodiment, a method for delivering a neurostimulation therapy includes enabling an external medical device including an inductive communication initiating device and an external antenna to apply a communication signal to the external antenna, receiving on an implantable antenna of an implantable medical device the communication signal inductively coupled between the external antenna and the implantable antenna, generating a voltage output signal at a voltage output of a rectifier in response to the inductively coupled communication signal, and providing the voltage output signal to a signal generator for powering generation of a therapeutic electrical stimulation signal delivered by electrodes to a neurostimulation site of a patient.

BRIEF DESCRIPTION OF THE DRAWINGS

FIG. 4A is a schematic diagram of an alternative exemplary embodiment of an IMD system including an IMD configured for NFC.

FIG. 4B is a schematic diagram of yet another exemplary embodiment of an IMD system including an IMD configured for NFC.

FIG. 8A is a plan view of an exemplary IMD including a communication antenna that is configured for receiving communication signals and as a fixation member for anchoring the IMD at a target implant site.

FIG. 8B is a sectional view of the IMD of FIG. 8A positioned in an implant tool.

FIGS. 9-16 are schematic views of various embodiments of exemplary IMD antennas configured as fixation members for anchoring the IMD at a target implant site.

DETAILED DESCRIPTION

Applicants have an appreciation that implantable medical device (IMD) technology is continually advancing as new applications are developed for automated therapy delivery in patients. Such advances may be further enhanced by using devices of reduced size and weight, which makes implantation of such devices less invasive and chronic use more comfortable for the patient. Additionally, applicants recognize that such enhancements such as improved power supply systems, wireless telemetry systems for communication with the implanted device, tools for performing implantation procedures, apparatus and methods for targeting a delivered therapy at desired location, and other system improvements can also enhance therapies in a manner that saves cost, conserves energy and minimizes any burden placed on the patient or clinician. Accordingly, Applicants recognize a need for improved, minimally-invasive implantable medical device systems and associated methods of use for providing patient monitoring and/or therapy delivery. Certain exemplary embodiments disclosed herein may obtain some or all of the aforementioned advantages and enhancements.

In the following description, references are made to illustrative embodiments. Various embodiments of an implantable neurostimulation (INS) system for delivering an electrical stimulation therapy to a targeted neural site are described. However, it is recognized that the various embodiments described herein may be implemented in numerous types of implantable medical device (IMD) systems, including, for example, implantable sensors or monitoring devices, implantable communication devices, and other types of implantable therapy delivery systems. The various embodiments of systems described herein and associated methods of use promote and facilitate minimally invasive IMD systems in which the incision size and time required to implant and anchor the device can be minimized. The IMD systems are designed to minimize cost, size and invasiveness of the device while providing efficacious therapy delivery (and/or accurate monitoring in a sensing-only device).

Figure 1:
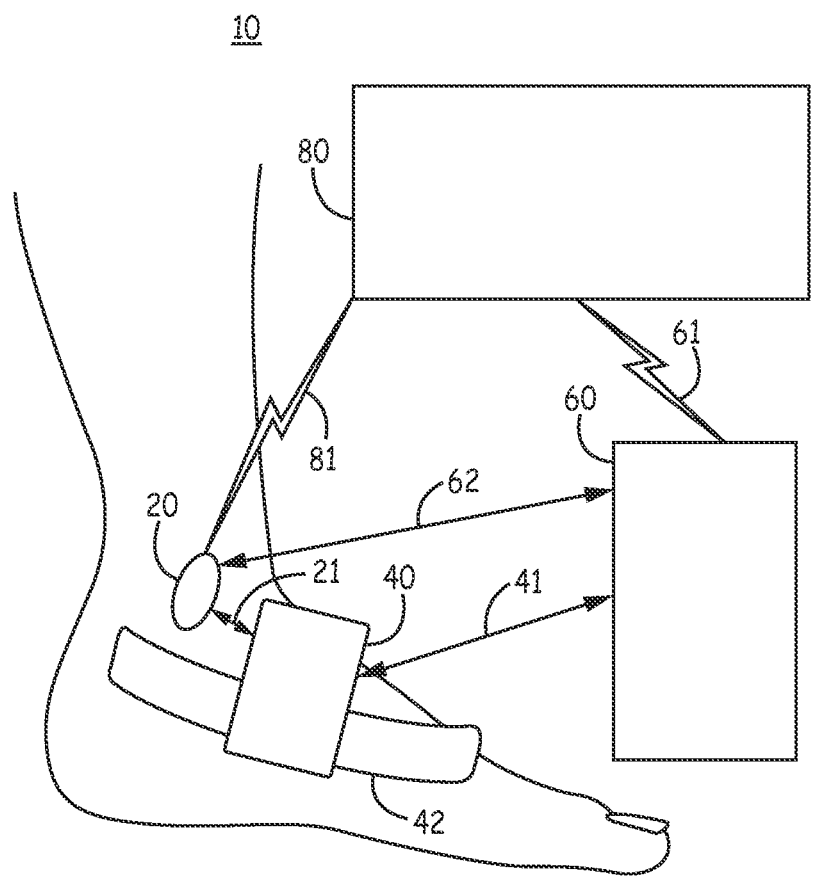
FIG. 1 is a schematic diagram of an exemplary minimally invasive IMD system capable of delivering a neurostimulation therapy.
Figure 1:
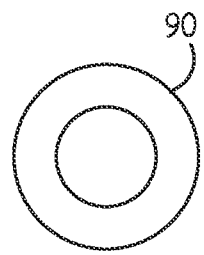

FIG. 1 is a schematic diagram of a minimally invasive INS system 10 capable of delivering a neurostimulation therapy. System 10 includes an IMD 20, an external device 40 enabled for transmitting signals to IMD 20, a patient programming device 60 enabled for bidirectional communication with IMD 20 and/or external device 40, and a physician programming device 80 according to one illustrative embodiment. In the illustrative embodiments described herein, communication between components included in the INS system 10 is configured to be bidirectional communication, however it is recognized that in some embodiments communication between two or more system components may be unidirectional.

IMD 20 includes circuitry for delivering neurostimulation pulses enclosed in a sealed housing and coupled to therapy delivery electrodes. In various embodiments, IMD 20 may include one or more of a primary battery cell, a rechargeable battery cell, and an inductively coupled power source for providing power for generating and delivering stimulation pulses and powering other device functions such as communication functions.

In some embodiments, IMD 20 is less than approximately 30 mm in length, or less than approximately 15 mm in length, and less than approximately 1 cc in volume. In illustrative embodiments, the term "approximately" as used herein may indicate a value of ±10% of a stated value or may correspond to a range of manufacturing specification tolerances. In other examples, IMD 20 may be less than approximately 10 mm in length and may be less than approximately 0.6 cc in volume. IMD 20 may be approximately 0.1 cc in volume in some embodiments. The examples described herein are not limited to a particular size and volume of IMD 20, but are generally implemented to enable the use of a reduced size device for minimally invasive implantation procedures and minimized discomfort to a patient. It is recognized, however, that the various IMD systems described herein may be implemented in conjunction with a wide variety of IMD sizes and volumes adapted for a particular therapy or monitoring application.

External device 40 may be a wearable device including a strap 42 or other attachment member(s) for securing external device 40 to the patient in operable proximity to IMD 20. When IMD 20 is provided with rechargeable battery cell(s), external device 40 may be embodied as a recharging unit for transmitting power, for example inductive power transmission from external device 40 to IMD 20. In this embodiment, programming device 60 may be a patient handheld device that is used to initiate and terminate therapy delivered by IMD 20 via a bidirectional wireless telemetry link 62. Alternatively, programming device 60 could be operated by a patient for communicating with wearable external device 40 via wireless link 41 to control therapy on and off times and other therapy control parameters, which are transmitted to IMD 20 via communication link 21. Programming device 60 may communicate with wearable external device 40 via a bidirectional wireless telemetry link 41 that may establish communication over a distance of up to a few feet or more, enabling distance telemetry such that the patient need not position programming device 60 directly over IMD 20 to control therapy on and off times or perform other interrogation or programming operations (e.g., programming of other therapy control parameters).

When IMD 20 includes primary cell(s), a wearable external device 40 may be optional. Programming of IMD 20 may be performed by the programming device 60, using near- or distance-telemetry technology for establishing bidirectional communication link 62 for transmitting data between programmer 60 and IMD 20. Programming device 60 may be used by a patient or clinician to set a therapy protocol that is performed automatically by IMD 20. Programming device 60 may be used to manually start and stop therapy, adjust therapy delivery parameters, and collect data from IMD 20, e.g. data relating to total accumulated therapy delivery time or other data relating to device operation or measurements taken by IMD 20.

When IMD 20 is configured as an externally powered device, external device 40 may be a power transmission device that is worn by the patient during a therapy session to provide power needed to generate stimulation pulses. For example, external device 40 may be a battery powered device including a primary coil used to inductively transmit power to a secondary coil included in IMD 20. External device 40 may include one or more primary and/or rechargeable cells and therefore may include a power adaptor and plug for re-charging in a standard 110V or 220V wall outlet, for example.

It is contemplated that in some embodiments the functionality required for transmitting power to IMD 20 when IMD 20 is embodied as a rechargeable or externally powered device and for programming the IMD 20 for controlling therapy delivery may be implemented in a single external device. For example, power transmission capability of external device 40 and programming capabilities of patient programmer 60 may be combined in a single external device, which may be a wearable or handheld device.

Physician programming device 80 may include increased programming and diagnostic functionality compared to patient programming device 60. For example, physician programming device 80 may be configured for programming all neurostimulation therapy control parameters, such as but not limited to pulse amplitude, pulse width, pulse shape, pulse frequency, duty cycle, and therapy on and off times. Patient programming device 60 may be limited to turning therapy on and/or off, adjusting a start time of therapy, and/or adjusting a pulse amplitude without giving access to the patient to full programming functions such that some programming functions and programmable therapy control parameters cannot be accessed or altered by a patient.

Physician programming device 80 may be configured to communicate directly with IMD 20 via wireless, bidirectional telemetry link 81, for example during an office visit. Additionally or alternatively, physician programming device 80 may be operable as remote programming instrument used to transmit programming commands to patient programming device 60 via a wired or wireless communication network link 61, after which patient programming device 60 automatically transmits programming data to IMD 20 via bidirectional telemetry link 62 (or via wearable external device 40 and link 21).

In some embodiments, the patient may be provided with a magnet 90 for adjusting operation of IMD 20. For example, application of magnet 90 may turn therapy on or off or cause other binary or stepwise adjustments to IMD 20 operations.

While IMD 20 is shown implanted along a portion of the lower leg of a patient, IMD 20 could be implanted at numerous sites according to patient need and the particular medical application. In the illustrative embodiment, IMD 20 is provided for stimulating the tibial nerve of the patient to treat overactive bladder syndrome and is merely one example of the type of medical application for which INS system 10 may be used. IMD 20 may be implanted superior to the flexor retinaculum, superficially to a deep fascia tissue layer that extends over the tibial nerve. Electrodes coupled to or carried by IMD 20 for delivering electrical stimulation to the tibial nerve may be positioned along the superficial surface of the deep fascia and/or penetrate through the deep fascia to be positioned in closer proximity to the tibial nerve. The signal generating portion of IMD 20, generating therapeutic nerve stimulation signals, is positioned superficially to the deep fascia and at an implant depth that enables IMD 20 to receive inductively coupled communication signals from external device 40, for example at an implant depth of 3 cm or less. In another example, IMD 20 may be implanted to deliver a stimulation therapy to muscles of the pelvic floor, such as periurethral muscles or the external urethral sphincter for treating symptoms of urinary incontinence or overactive bladder syndrome. In other examples, IMD 20 may be deployed for delivering neurostimulation therapy to an acupuncture point for treatment of a symptom associated with the acupuncture point. IMD 20 may be implemented in an INS system for providing numerous types of neurostimulation therapies, such as for pain control, autonomic nervous system modulation, tremor, functional electrical stimulation, and more.

Figure 2:
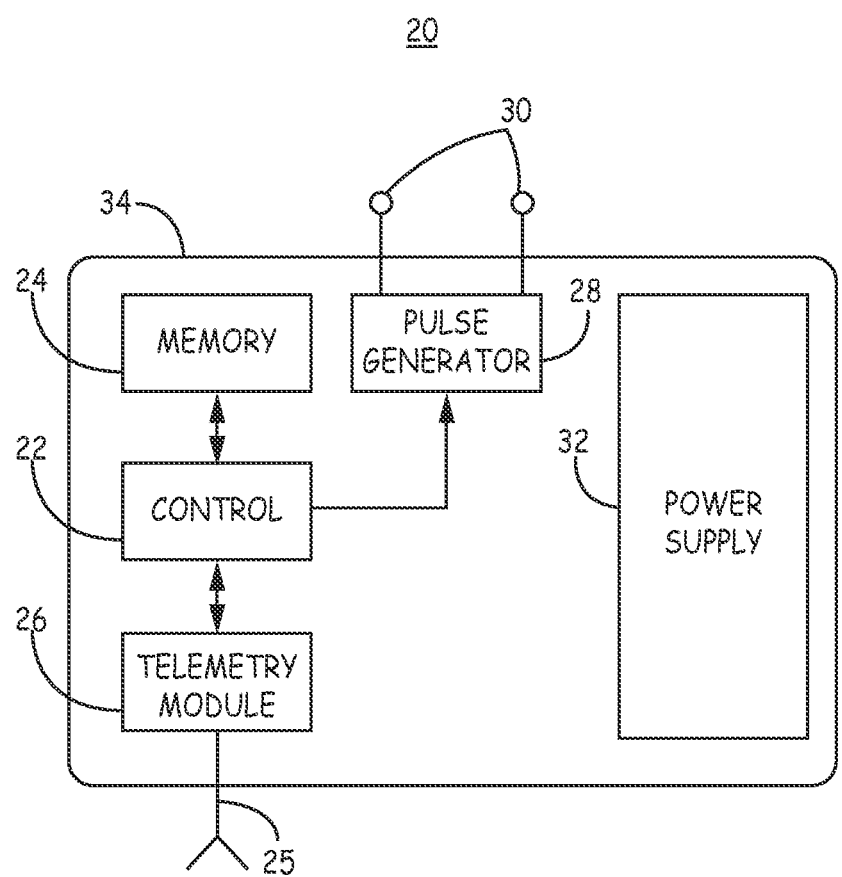
FIG. 2 is a functional block diagram of the IMD shown in FIG. 1 according to one exemplary embodiment.

FIG. 2 is a functional block diagram of IMD 20 according to one embodiment. IMD 20 includes a housing 34 enclosing a control unit 22 and associated memory 24, a telemetry module 26, and a pulse generator 28 coupled to electrodes 30. IMD 20 includes a power supply 32, which as described above may include any of a primary battery cell, a rechargeable battery cell, and/or a secondary coil of an externally powered system.

Control unit 22 may include any one or more of a microprocessor, a controller, a digital signal processor (DSP), an application specific integrated circuit (ASIC), a field-programmable gate array (FPGA), or equivalent discrete or integrated logic circuitry. In some examples, control unit 22 may include multiple components, such as any combination of one or more microprocessors, one or more controllers, one or more DSPs, one or more ASICs, or one or more FPGAs, as well as other discrete or integrated logic circuitry. The functions attributed to control unit 22 herein may be embodied as software, firmware, hardware or any combination thereof. In one example, a neurostimulation therapy protocol may be stored or encoded as instructions in memory 24 that are executed by control unit 22 to cause pulse generator 28 to deliver the therapy via electrodes 30 according to the programmed protocol.

Memory 24 may include computer-readable instructions that, when executed by control unit 22, cause IMD 20 to perform various functions attributed throughout this disclosure to IMD 20. The computer-readable instructions may be encoded within memory 24. Memory 24 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, with the sole exception being a transitory propagating signal.

Telemetry module 26 and associated antenna 25 are provided for establishing bidirectional communication with wearable external device 40, patient programmer 60 and/or physician programmer 80. Examples of communication techniques used by IMD 20 and an external device 40, patient programmer 60 and/or physician programmer 80 include low frequency or radiofrequency (RF) telemetry, which may be an RF link established via Bluetooth, WiFi, Near-Field Communication (NFC), or MICS, for example. Antenna 25 may be located within, along or extend externally from housing 34.

In one embodiment, telemetry module 26 is implemented as an NFC target device capable of receiving NFC signals and harvesting power from the carrier signal. One example of a commercially available NFC target device is the M24LR16E-R dual interface EEPROM, available from STMicroelectronics, Huntsville, Ala., USA.

Electrodes 30 may be located along an exterior surface of housing 34 and are coupled to pulse generator 28 via insulated feedthroughs. In other embodiments, electrodes 30 may be carried by a lead or insulated tether electrically coupled to pulse generator 28 via appropriate insulated feedthroughs or other electrical connections crossing sealed housing 34. In still other embodiments, electrodes 30 may be incorporated in housing 34 with externally exposed surfaces adapted to be operably positioned in proximity to a targeted nerve and electrically coupled to pulse generator 28.

Figure 3:
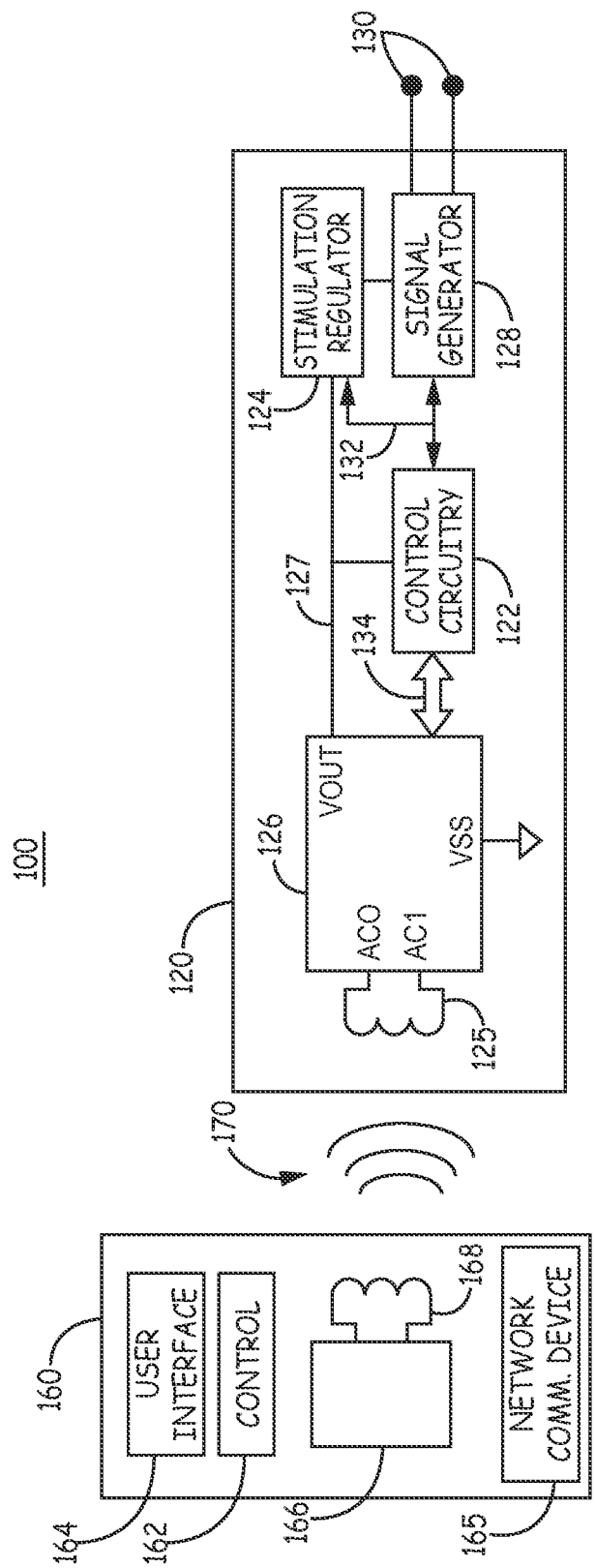
FIG. 3 is a schematic diagram of one exemplary embodiment of an implantable neurostimulation (INS) system incorporating Near-Field Communication (NFC) for wireless communication and power transfer to an IMD.

FIG. 3 is a schematic diagram of one embodiment of an INS system 100 incorporating Near-Field Communication (NFC) for wireless communication and power transfer to an IMD 120. IMD 120 includes NFC target device 126 and associated implantable antenna 125. IMD 120 further includes control circuitry 122, which may be implemented as a microprocessor and associated memory or other control circuitry as described above in conjunction with FIG. 2. Signal generator 128 receives a regulated voltage signal from regulator 124 and generates stimulation pulses or other desired stimulation signal waveforms or shapes to be delivered to a targeted tissue site via electrodes 130.

NFC target device 126 harvests power from an NFC communication signal 170 received on implantable antenna 125 tuned to the NFC carrier frequency standard of 13.56 MHz. Through inductive power harvesting, NFC target device 126 provides a rectified voltage output signal Vout 127. The output signal Vout 127 provides the power needed for signal generator 128 to generate a neurostimulation signal. In one embodiment, the Vout signal 127 is regulated by regulator 124 and the regulated signal is used to generate stimulation output signals by signal generator 128. In some embodiments, the output signal Vout 127 is the sole power source providing power to signal generator 128 for generating a neurostimulation signal. The Vout signal 127 may be provided to stimulation regulator for regulating the voltage and providing a voltage signal to signal generator 128 at or above the input voltage of Vout signal 127.

Vout 127 may also be provided as a power source to control circuitry 122. In this way, the telemetry communication module including NFC target device 126 provides power to signal generator 128 for therapy delivery as well as all other functions of IMD 120. Control circuitry 122, which may be embodied as a microprocessor, receives the rectified Vout signal 127 from NFC target device 126 and communication data on a data bus 134. Control circuitry 122 provides control signals to (and may receive signals back from) stimulation regulator 124 and signal generator 128 on signal line 132. In this way, control circuitry 122 may use information and power received from NFC target device 126 to control stimulation regulator 124 and signal generator 128 to deliver a neurostimulation therapy according to desired therapy parameters.

NFC is one commercially available, industry standardized short-range inductive communication technology that could be implemented in target device 126 and external device 160, however other examples of inductive communication technology that could be used include a Passive Low Frequency Interface (PaLFI) device which operates at 135 kHz, such as the TMS37157 Target Board available from Texas Instruments, Dallas Tex., USA, or other radio frequency identity (RFID) devices, for example operating at a frequency of 125 kHz. Other standard protocols may operate in the range of 100-200 kHz. Frequencies above and/or below this range are contemplated, with a chosen frequency being a balance of regulatory restrictions, biological interactions, and transmission efficiency among other considerations. Implementing an industry communication standard target device 126 can reduce the cost of IMD 120 and provide flexibility in using standard commercially available external devices for inductive power transfer and communication with IMD. It is recognized, however, that a custom inductive communication telemetry unit may be utilized for communication transmissions and for power transmission rather than a commercially available target device.

External device 160 may be embodied as a wearable or handheld device that is positioned in close proximity to IMD 120. External device 160 includes a control module 162, which may be a microprocessor and associated memory, a user interface 164 and an NFC initiating device 166 and associated antenna 168.

A transmitted signal 170 may be an amplitude shift keyed (ASK), frequency shift keyed (FSK) or phase shift keyed (PSK) signal including encoded data that is decoded by IMD 120 and used for controlling IMD operations. At times when data transfer is required, the carrier signal is modulated according to a selected modulation and encoding technique to include one or more intervals of communication data. At times when data transfer is not required, the NFC signal 170 may be solely a carrier signal that is used by NFC target device 126 for power harvesting. The NFC signal 170 may therefore be transmitted for the full duration of a therapy session, which could last from several seconds to several minutes, up to one hour or more depending on the therapy application, even when data communication is not needed. At other times, the NFC signal 170 may include data being transmitted to IMD 120 during the therapy session by modulating the carrier signal, with simultaneous power harvesting (i.e. during both carrier signal only intervals and data transfer intervals) for providing a voltage signal to the signal generator for generating a therapeutic electrical stimulation signal delivered by electrodes 130. "Communication data" as used herein may refer to identification or authentication data, therapy control parameters, commands including interrogation commands, or any other information or data being transmitted to IMD 120 via modulation of a carrier signal to encode the data in the inductively coupled signal.

While implantable device 126 is referred to as a "target" device, it is recognized that at times device 126 is transmitting data to external device 160 and at other times device 126 is receiving a signal from external device 160 in bidirectional communication. Data transferred to external device 160 may include any of device diagnostic data, device identity data, therapy related data, and signals sensed or acquired by IMD 120.

In one embodiment, whenever external device 160 is within communication range of IMD 120, e.g. within several centimeters, the communication link 170 is established and IMD 120 is powered to perform device functions. In one embodiment, initiating device 166 and target device 126 are configured to operate when within approximately 3 cm of each other for transmitting communication data. When inductive coupling between primary external coil, i.e. external antenna 168, and secondary implantable coil, i.e. implantable antenna 125, is performed for power transfer, the initiating and target devices 166 and 126 may be up to 2 cm apart in one example. Stimulation therapy may be initiated by IMD 120 upon receiving a valid carrier signal or at a controlled time as determined by control circuitry 122. Accordingly, in one embodiment, a user may position external device 160 within communication range of IMD 120 to start therapy and move external device 160 out of communication range of IMD 120 to stop therapy.

External device 160 may include a user interface 164 that allows a user to interact with device 160 for initiating a therapy session and/or data communication session and/or for adjusting therapy control parameters. Example user interfaces may include push-buttons, dials, a touch screen, voice activation, a mechanical actuator responding to tapping on the device, or any combination thereof. In one example, external device 160 is embodied as a smart phone or other personal handheld device including applications stored in and executed by control module 162 for receiving user input via a touch screen and for controlling NFC initiating device 166.

External device 160 may include a network communication device 165 to enable device 160 to send and receive data over a local or wide area network or a cellular network. In this way, device 160 may be controlled remotely by another networked device as further described below. Device 160 may also send data to a networked device, which may be for example, a physician computer, cell phone, or central database to allow remote monitoring of data acquired and transmitted by IMD 120.

FIG. 4A is a schematic diagram of an alternative embodiment of an IMD system 100' including an IMD 150 configured for NFC. External device 160 generally corresponds to device 160 shown in FIG. 3. IMD 150 generally includes control circuitry 122, signal generator 128 coupled to electrodes 130 and a regulator 124 as described above. IMD 150, however, includes a non-rechargeable primary cell 152 or other non-rechargeable energy storage device. Primary cell 152 is coupled to control circuitry 122 and regulator 124 for powering IMD control functions and therapy delivery functions. Vout of the NFC target device 126 is not shown coupled to other IMD components as described in conjunction with FIG. 3. In some embodiments, however, Vout may be selectively coupled to stimulation regulator 124 to provide back-up power in case primary cell 152 is near end-of-life. In other embodiments, control circuitry 122 and stimulation regulator 124 may be powered by either energy harvested from the NFC carrier signal (Vout 127) or the primary cell 152 or a combination thereof.

NFC device 126 and associated antenna 125 is used for communication with external device 160 for setting therapy control parameters or other data transfer. The NFC device 126 may be powered by power harvested from the transmitted signal 170 or primary cell 152 may be coupled to NFC device 126 as a power source. Stimulation parameters or other control parameters may be transmitted to IMD 150 via NFC signal 170, but external device 160 need not remain within communication range of IMD 150 throughout a therapy session.

FIG. 4B is a schematic diagram of yet another embodiment of an IMD system 100" including external device 160 (as described previously) and IMD 154 configured for NFC. In other variations, IMD 154 may include a rechargeable cell 156 or other rechargeable energy storage device for powering some or all IMD functions. Vout 127 from NFC target device 126 may be coupled to rechargeable cell 156 as a power source for recharging cell 156. Control circuitry 122 and stimulation regulator 124 may be powered by either energy harvested from the NFC carrier signal (Vout 127) or the rechargeable cell 156 or a combination thereof.

Rechargeable cell 156 may be recharged any time the external device 160 is within communication range of IMD 150. Data may be transferred via signal 170. Therapy delivery may occur without requiring the external device 160 being maintained within communication range of IMD 154 when signal generator 128 is configured to receive power from rechargeable cell 156.

Figure 5:
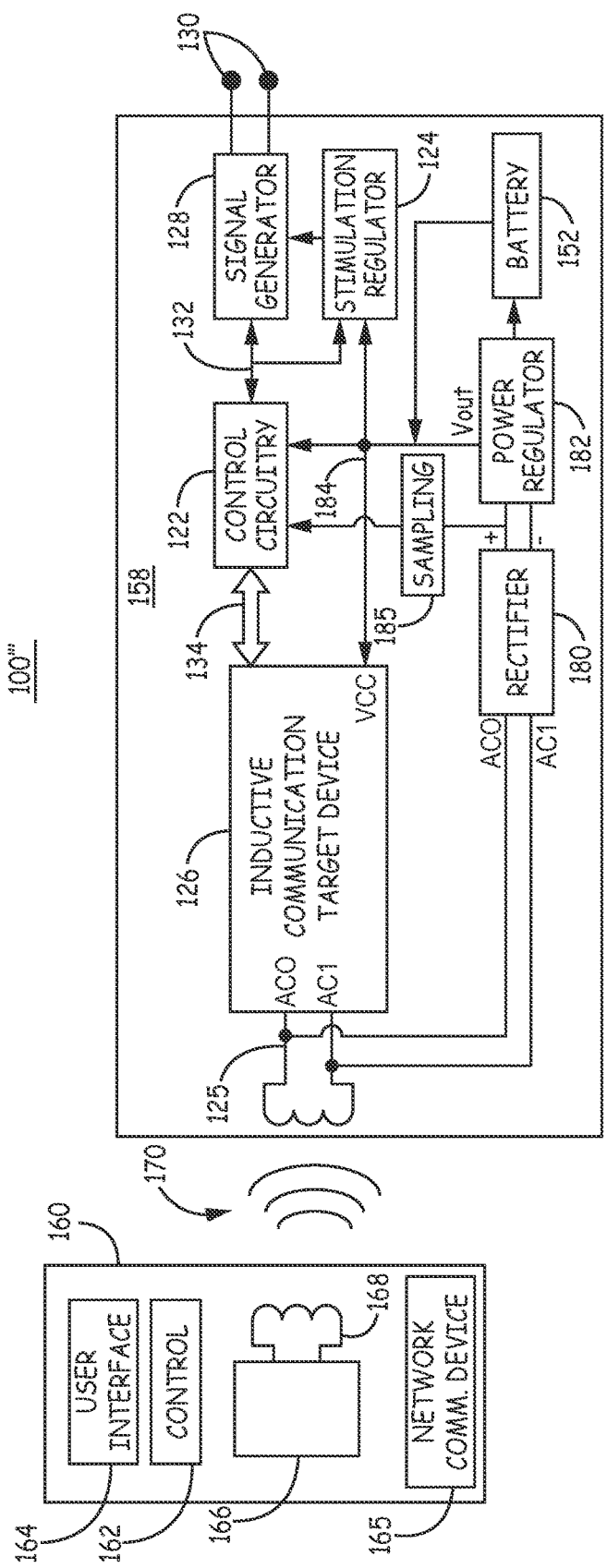
FIG. 5 is a schematic diagram of another exemplary embodiment of an INS system incorporating inductive communication and power harvesting in an IMD.

FIG. 5 is a schematic diagram of an IMD 158 for use in an INS system 100''' incorporating inductive communication and power transfer according to an alternative embodiment. In the embodiments shown in FIGS. 3, 4A and 4B, the target device 126 provides the rectified Vout signal harvested from the inductively coupled communication signal 170. In an alternative embodiment, the inductively coupled communication signal 170 received by implantable antenna 125 is provided to a rectifier 180 coupled to antenna 125 in parallel to target device 126. Thus the communication signal 170 provides the inductively coupled signal that is rectified for providing a power output signal to power other IMD components, but the rectification and regulation of the signal 170 is performed in parallel to receiving and analyzing the signal 170 for decoding communication data (when present). The parallel arrangement of the communication target device 126 and power harvesting components including rectifier 180 and power regulator 182 can increase power conversion efficiency while still utilizing a common inductively coupled signal and implantable secondary coil for both communication and power reception.

Rectifier 180 may be embodied as a full wave Schottky rectifier or other full wave rectifier. Rectifier 180 receives the inductively coupled signal from antenna 125 and provides a rectified output signal to power regulator 182. Power regulator 182 may include one or more of each of a filter, a voltage regulator, a current limiter, protection circuitry and other components to provide a Vout signal 184 that at least provides power to signal generator 128 for producing a neurostimulation signal delivered by electrodes 130.

As shown in FIG. 5, the Vout signal 184 may be provided to a stimulation regulator 124, which provides a voltage signal to signal generator 128 used to deliver the neurostimulation therapy signal to electrodes 130. In other embodiments, stimulation regulator 124 and power regulator 182 may be integrated in a single regulator module that provides a regulated Vout signal to signal generator 128. Power regulator 182 and/or stimulation regulator 124 may be configured as a booster to provide an output signal having a voltage equal to or greater than the rectified output signal received from rectifier 180.

Vout signal 184 may additionally be provided to control circuitry 122 to power a microprocessor and other control circuitry components operating to control IMD functions. As described above, control circuitry 122 receives communication data from target device 126 on a data bus 134 and provides control signals to signal generator 128 and stimulation regulator 124 on signal lines 132.

Communication target device 126 may be powered by internally harvesting power from inductively coupled signal 170 and generating a rectified voltage signal to power internal components of target device 126. In this embodiment, target device may have no input coupled to the Vcc power input. Additionally or alternatively, the communication target device 126 receives the Vout signal 184 from power regulator 182 to provide power to the target device 126 for powering communication functions or to supplement power internally harvested by target device 126 for powering communication functions. Thus, the Vout signal 184 generated in parallel to communication signal data provided on bus 134, both in response to inductively coupled communication signal 170, may be used in combination with power harvesting performed by target device 126, to provide an overall power source to components of IMD 158.

Power harvested from inductively coupled signal 170 may be the sole power source for IMD 158 components. Alternatively, in some embodiments IMD 158 may include a rechargeable battery or other charge storage device 152. Battery 152 may receive an output signal from power regulator 182 for charging battery 152. Charging of battery 152 may occur at times therapy is not being delivered by signal generator 128 or may occur simultaneously. Battery 152 may provide an output signal that is used to supplement the Vout signal 184 for powering IMD components, used as a back-up power source when the Vout signal 184 is not available, or used to power some components of IMD 158 while other components are powered by Vout signal 184. As indicated above, battery 152, or another rechargeable energy storage device, is optional.

In some embodiments, control circuitry 122 samples a signal correlated to the power harvested from inductively coupled signal 170. A sampling circuit 185 may be provided to measure a voltage signal output from rectifier 180 as shown. The control circuitry 122 may respond to a measurement of the rectifier output signal by altering control of signal generator 128, stimulation regulator 124, or provide a feedback control signal to the initiating device 166 via data bus 134 and target device 126. A drive signal applied to external antenna 168 may be adjusted to adjust inductively coupled signal 170 as needed to maintain the output of rectifier 180 in a desired range. In alternative embodiments, sampling circuit 185 may sample or measure the Vout signal from power regulator 182 or the inductively coupled signal between antenna 125 and rectifier 180 for providing control circuitry 122 with a feedback control signal for use in controlling IMD functions based on power available and/or providing a feedback control signal to initiating device 166.

Figure 6:
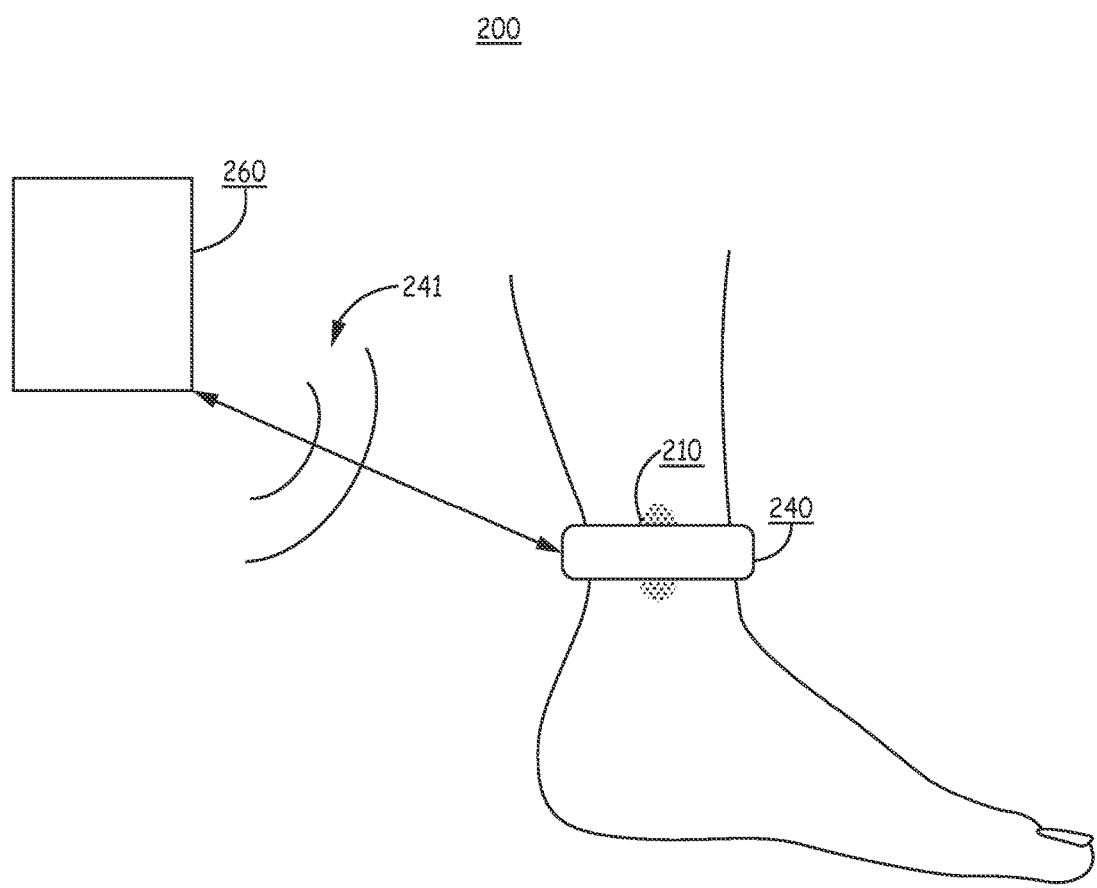
FIG. 6 is a schematic diagram of an IMD system according to another exemplary embodiment.

FIG. 6 is a schematic diagram of an IMD system 200 according to another embodiment. IMD system 200 includes a patient device 260, a wearable external coupling device 240, and IMD 210. External coupling device 240 is enabled to transmit data and/or power to IMD 210 via low frequency wireless communication via associated transceiver devices, such as NFC, PaLFI, or other RFID devices or other short-range, near field communication devices, e.g. as described in conjunction with FIG. 3. External coupling device 240 functions as an interface between patient device 260 and IMD 210 such that a patient or other user is not required to interact directly with wearable device 240. For example, if a patient wants to initiate therapy or adjust therapy parameters, the patient can conveniently and discreetly interact with a handheld device 260, for example, instead of having to reach toward and interact with wearable device 240, which may be under clothing or not easily accessible.

Wearable device 240 is configured for bidirectional communication with patient device 260, which may be a handheld device such as a dedicated system device, a smart phone, tablet device, or a personal computer such as a notebook or laptop computer. Wearable external device 240 and patient device 260 are configured to communicate via a wireless link 241 on a local area network (LAN) such as a network established using WiFi wireless technology, BLUETOOTH® wireless technology, or ZIGBEE® wireless technology.

A patient using device 260 may transmit a command to turn a therapy on or off, instantaneously or at a scheduled time, adjust an intensity or strength of the therapy up or down, or adjust other therapy control parameters as directed by a clinician or according to patient need. Patient device 260 transmits the commands or data to wearable external device 240, which in turn transmits the data to IMD 210, immediately or at a scheduled time. External device 240 will establish a telemetry session with IMD 210 at the appropriate time to enable power transfer from an initiating NFC device included in external device 240 to a target device included in IMD 210 to start therapy delivery according to a scheduled time or in response to a command received from patient device 260. Likewise, at an appropriate time, external device 240 will terminate a telemetry session to end the power transfer and thereby terminate the therapy. Using patient device 260, a patient may conveniently control and interact with IMD 210 via wearable device 240.

Figure 7:
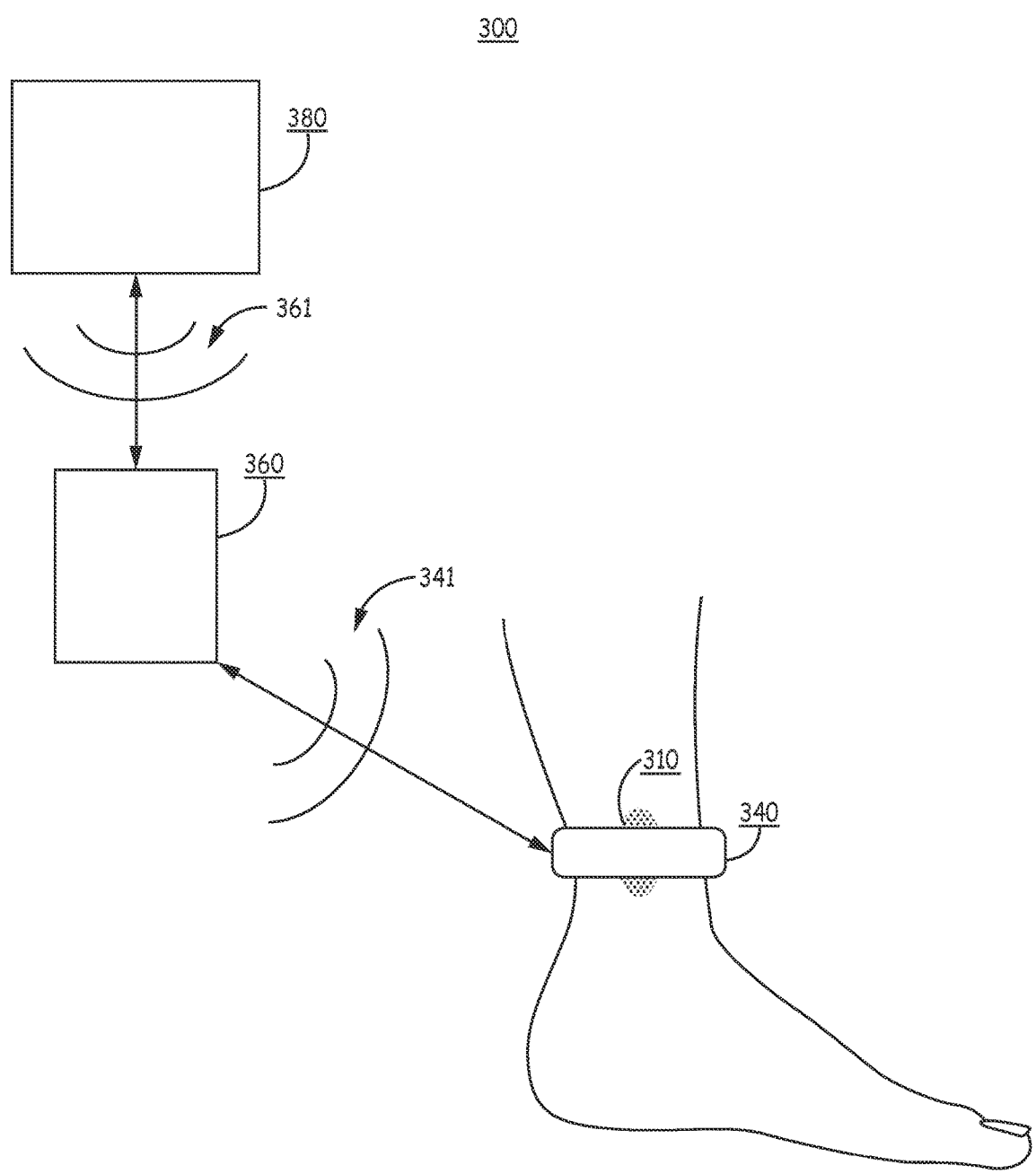
FIG. 7 is a schematic diagram of yet another exemplary embodiment of an IMD system.

FIG. 7 is a schematic diagram of yet another embodiment of an IMD system 300. System 300 includes an IMD 310, a wearable external device 340, an external patient device 360, and a remote patient management device 380. In this embodiment, a clinician, technician, or other expert may control IMD 310 remotely using remote patient management device 380. Remote device 380 and patient device 360 are enabled to communicate via a communication link 361 over a wide area network (WAN) using, for example, the standard Transmission Control Protocol/Internet Protocol (TCP/IP).

A user interacting with remote device 380, which may be a personal computer, a network-enabled device programmer, a handheld device, a smart phone, or other network enabled device, is able to adjust therapy control parameters programmed in IMD 310, remotely turn IMD 310 on or off, or retrieve data acquired by patient device 360, external coupling device 340, and/or IMD 310. Any or all of the devices 310, 340, and 360 may accumulate therapy-related, patient-related and/or device diagnostic data that may be retrieved by remote patient management device 380.

After a programming change or command is entered using a user interface of remote patient management device 380, the programming change or command is encoded and transmitted via network link 361 to patient device 360, which in turn transmits the encoded data to wearable device 340 via communication link 341, e.g. via a LAN or WAN. The encoded data is then transmitted to IMD 310 via coupling device 340 using NFC or another short range RF communication protocol. The data may be transmitted immediately or at a scheduled therapy time when both data transmission and power transmission is accomplished simultaneously.

FIG. 8A is a plan view of an IMD 400 including a communication antenna 414 that is configured for receiving communication signals and as a fixation member for anchoring the IMD 400 at a target implant site. IMD 400 may include an NFC target device as described above or more generally may include any wireless telemetry module as described in conjunction with FIGS. 1 and 2 for communicating with an external device and/or for harvesting power from a communication carrier signal. In order to facilitate a minimally invasive surgery for implanting the IMD 400, the IMD is generally having small outer dimensions and volume as described above.

Use of an antenna as both a fixation member and a communication antenna helps to reduce overall device size, reduce manufacturing cost, and facilitate minimally invasive implant procedures in which the incision size and time required to implant and anchor the device can be minimized. The IMD 400 may be an "injectable" device where the IMD 400 is loaded into a catheter, syringe body or other delivery device and a plunger or other release mechanism is used to insert the IMD into a tissue pocket or other cavity to deploy the device at a target site. Since an implanting clinician may not have direct open access to the target implant site, fixation of the IMD at the implant site by a fixation member that is automatically deployed upon injecting the IMD 400 can reduce implantation time, incision size, and skill required for implanting the device.

In FIG. 8A, IMD 400 includes a sealed housing 410 enclosing electronic circuitry. An antenna 414, shown as a dipole antenna having a first portion 414a and a second portion 414b, extends from housing 410. One dipole 414a or 414b of antenna 414 is electrically coupled to electronic circuitry enclosed within housing 410 via an electrical feedthrough extending through housing 410, and the other dipole is coupled to ground, which may be housing 410. Antenna 414 is mechanically coupled to housing 410 by an overmold 412 that anchors proximal ends 416a and 416b to IMD housing 410 and reduces any strain on the feedthrough portions of antenna 414. Overmold 412 may be a biostable thermoplastic or thermoset polymer such as polysulfone, polyurethane, liquid crystal polymer, polyether ether ketone (PEEK), epoxy, diamond like carbon, silicone or PURSIL® biostable silicone polyether, available from DSM, Berkeley Calif., or any combination thereof. Overmold 412 is molded over a proximal portion of antenna 414 and at least a portion of housing 410 to embed proximal ends 416a, 416b and provide a secure mechanical coupling of antenna 414 to IMD housing 410.

Antenna 414 is formed of a biostable metal or alloy, such as titanium or a titanium alloy. In some embodiments, antenna 414 may be formed from a shape memory metal, such a Nitinol, an alloy of nickel and titanium. Each dipole 414a and 414b, collectively antenna 414, includes a bend or curve 415 that acts to anchor antenna 414 in a tissue pocket by pressing against the surrounding tissue of the pocket or causing distal dipole ends 418a and 418b to extend into surrounding tissue such that tissue is "grabbed" or "captured" within the curve or bend 415 of the dipole 414a, 414b. Each dipole 414a and 414b is shown having a preformed normally "C"-shaped position in FIG. 8A that includes a first proximal portion extending from overmold 412 longitudinally away from IMD housing 410 along a long axis of IMD 400, a midportion having curve 415 that curves back toward IMD housing 410, and distal antenna ends 418a and 418b that extend back in the direction of lateral sides of IMD housing 410.

In other embodiments, dipoles 414a and 414b may curve or bend to extend distal antenna ends 418a and 418b laterally outward, away from IMD 400, rather than inwardly as shown in FIG. 8A. Dipoles 414a and 414b may curve or bend substantially within a major plane of IMD 400 or may extend out of the major plane of IMD 400. The dipoles 414a and 414b may include one or more bends or curves to form a variety of geometries, such as an S-shape, U-shape, L-shape, spiral, serpentine or other curving or bending geometry that enables antenna 414 to promote stable positioning of IMD 400 at a desired implant site and deter migration of IMD 400. In some embodiments, antenna 414 may provide passive fixation upon implant and become encapsulated by tissue over time providing chronic stability of the IMD position.

It is contemplated that an antenna 414 that functions as a fixation member may be formed as half of a dipole in some embodiments such that only one of dipoles 414a or 414b extend out from overmold 412, and may be coupled to ground. It is further contemplated that antenna 414 may include one or more barbs, hooks, flanges or other tissue engaging structure(s) extending therefrom to further improve the fixation of IMD 400.

In each of the antenna embodiments described herein, the antenna is tuned for receiving a carrier frequency of a communication signal. As such, the antenna length may be selected based on the frequency of the carrier signal of the communication protocol being used.

FIG. 8B is a sectional view of an implant tool 402 for delivering IMD 400 of FIG. 8A. Implant tool 402 includes a body 404 defining a lumen 406 for retaining IMD housing 410. In various embodiments, tool body 404 may be a syringe body, a catheter body, or any other tool body including a cavity or lumen for retaining IMD housing 410 prior to deployment, an opening 405 for passage of IMD housing 410, and a plunger 408 or other release mechanism to cause IMD housing 410 to pass through opening 405 during deployment. Tool 402 is shown to include a plunger 408 for injecting IMD housing 410 out distal opening 405 of body 404. When constrained within lumen 406, antenna 414 is held in an undeployed position, generally aligned longitudinally with IMD housing 410 such that IMD housing 410 with antenna 414 may be implanted through a small skin incision.

As IMD housing 410 is advanced out distal tool opening 405, antenna dipoles 414a and 414b, no longer constrained by body 404, will assume the deployed position as shown in FIG. 8A to anchor IMD 400 at a target implant site.

FIGS. 9-16 are schematic views of various embodiments of IMD antennas configured as fixation members for anchoring the IMD at a target implant site. FIG. 9 is a top view of an IMD 420 including a magnetically-coupled loop antenna 424 having a proximal portion 426 mechanically coupled to the IMD housing 421 by an overmold 422 as described above. The proximal portion 426 is electrically coupled to a feedthrough extending through IMD housing 420 to connect antenna 424 to IMD circuitry. A loop portion 425 of antenna 424 may extend away from IMD 420 substantially in a major longitudinal plane of IMD 420. Alternatively, a loop portion may bend or curve to extend out of the major longitudinal plane of IMD 420, as shown by the loop antennas 424' and 424" coupled to respective IMDs 420' and 420" in FIGS. 10 and 11. When an antenna loop is included on opposing ends of the IMD as shown in FIGS. 9-11, each loop may bend or curve in the same or different directions or planes relative to IMD 420. The loop antenna 424 may be constrained in a narrowed, undeployed position within an implant tool or catheter and assume a widened circular or elliptical shape upon deployment into a tissue pocket, outside the constraint of an implant tool or catheter.

Figure 12:
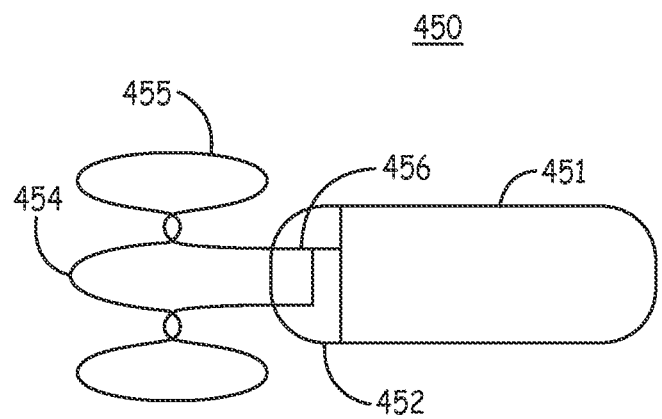

FIG. 12 is a top plan view of an IMD 450 including an antenna 454 configured as a fixation member according to an alternative embodiment. Antenna 454 is mechanically coupled to IMD housing 451 by a biostable polymeric overmold 452. A proximal end 456 of antenna 454 is electrically coupled to IMD circuitry via a feedthrough extending through housing 451 and is embedded in overmold 452. Antenna 454 includes a stent-like woven portion 455 that may be formed similar to an expandable vascular stent. Woven portion 455 may be formed using a number of weave patterns, such as D-shaped or U-shaped pattern. The stent-like woven portion may be formed to extend in two dimensions, such that it lies substantially flat in a major plane that may be approximately co-planar or parallel to a major plane of IMD 450, approximately perpendicular to a major plane of IMD 450, or in a plane that intersects with the major plane of IMD 450 at any angle.

In some embodiments, stent-like woven portion 455 may be formed to extend in three dimensions such that antenna 454 forms a woven ring or basket-like structure. When antenna 454 is formed from a shape memory metal such as nitinol, antenna 454 may be compressed to a relatively small size and constrained within an implant tool or catheter and then expand to a deployed position when released from the implant tool. The expansion to a deployed position provides anchoring of IMD 450 within a tissue pocket at an implant site.

Figure 13:
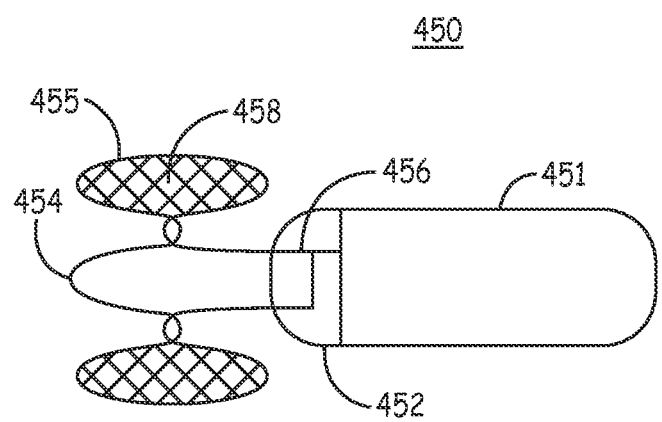

Tissue encapsulation of antenna 454 over time will provide additional fixation of IMD 450. In some embodiments, a mesh 458 or woven fabric may extend within or between weave loops of antenna 454, as shown in FIG. 13, to promote tissue ingrowth and anchoring of IMD 450.

Figure 14:
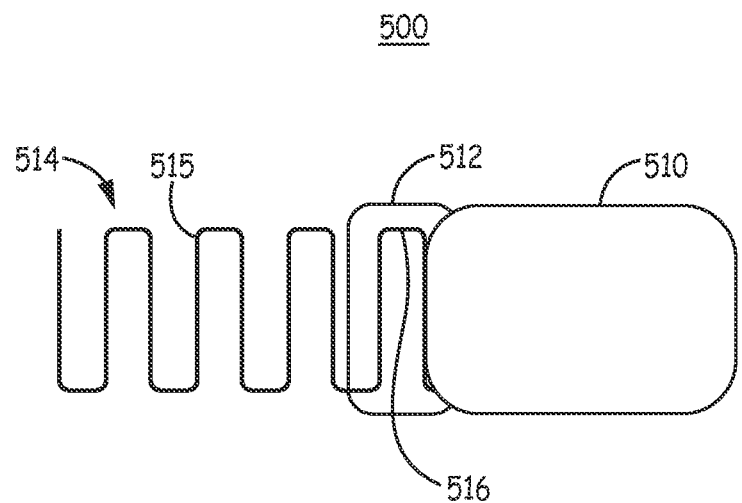

FIG. 14 is a top plan view of an IMD 500 including an antenna 514 having a serpentine portion 515 configured for providing fixation of IMD 500 at a target implant site. A proximal portion 516 of antenna 514 is mechanically coupled to IMD housing 510 by overmold 512 and electrically coupled to IMD circuitry via a feedthrough extending through housing 510. Overmold 512 may embed a portion of serpentine portion 515. Serpentine portion extends away from IMD housing 510 to provide passive fixation of IMD 500.

Figure 15:
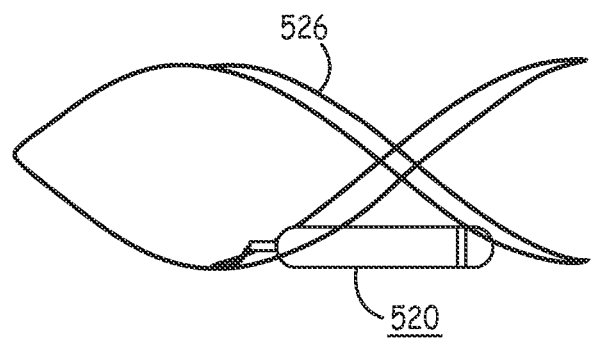

FIG. 15 is a perspective view of an IMD 520 including a magnetically coupled loop antenna 526 having a three-dimensional sinusoidal shape. The antenna 526 curves such that the sinusoidal shape extends substantially back over IMD 520, but antenna 526 may alternatively extend away from IMD 520.

Figure 16:
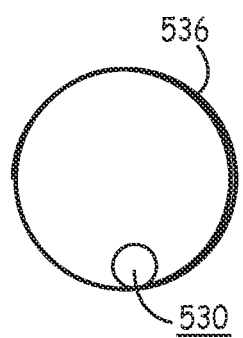

FIG. 16 is an end view of an IMD 530 including an electromagnetically coupled loop antenna 536 having a cylindrical shape, which may correspond to an end view of the sinusoidal shape shown in FIG. 15. In the illustrative embodiment, antenna 536 loops around IMD 530 such that IMD 530 is positioned within the loop antenna, however in other embodiments IMD 530 may be positioned outside a circular or cylindrical loop antenna 536. It is further contemplated that the IMD 530 may be substantially centered in a circular or cylindrical loop antenna 536 and that a loop antenna 536 may include one or more circular or elliptical loops extending in one or more planes.

Thus, various embodiments of a minimally invasive IMD system have been presented in the foregoing description with reference to specific embodiments. The various communication, power and fixation features of an IMD described herein may be implemented in any combination other than the particular combinations shown in the illustrative embodiments, which may include adding or omitting some features. It is appreciated that various modifications to the referenced embodiments may be made without departing from the scope of the disclosure as set forth in the following claims.

The invention claimed is:

1. A medical device system, comprising:
an external medical device comprising an inductive communication initiating device coupled to an external antenna; and
an implantable medical device comprising:
a control unit;
a signal generator for generating a therapeutic electrical stimulation signal;
a plurality of electrodes coupled to the signal generator for delivering the electrical stimulation signal to a neurostimulation site of a patient;
an inductive communication target device;
an implantable antenna coupled to the target device for receiving a communication signal inductively coupled between the external antenna and the implantable antenna;
a rectifier coupled to the implantable antenna for receiving the inductively coupled communication signal and having a voltage output providing a voltage output signal in response to receiving the inductively coupled communication signal; and
a sampling circuit coupled to the control unit and to a signal line for measuring a voltage signal correlated to the voltage output, and for providing the control unit with a feedback control signal based on the voltage signal,
the voltage output being a sole power source coupled to the signal generator to provide the voltage output signal to the signal generator for generating the therapeutic electrical stimulation signal delivered by the plurality of electrodes, the control unit configured to alter control of the signal generator based on the feedback control signal.

2. The system of claim 1, wherein the voltage output is further coupled to at least one of the control unit and the target device to provide the voltage output signal to power the at least one of the control unit and the target device.

3. The system of claim 2, wherein the voltage output signal being a sole signal for powering functions of the implantable medical device.

4. The system of claim 1, wherein the rectifier comprises a rectifier included in the target device.

5. The system of claim 1, wherein the implantable device further comprises a rechargeable energy storage device, the voltage output being further coupled to the rechargeable energy storage device for recharging the energy storage device.

6. The system of claim 1, wherein the communication signal comprises a carrier signal, the external medical device enabled to apply the carrier signal to the external antenna for inductively coupling the carrier signal between the external antenna and the implantable antenna for generating the voltage output signal for a full duration of a neurostimulation therapy session.

7. The system of claim 6, wherein the external medical device is further enabled to modulate the carrier signal to transmit the communication signal comprising an interval of communication data during the therapy session, the rectifier configured to receive the inductively coupled signal during the interval of communication data to provide the voltage output signal in response to the inductively coupled signal.

8. The system of claim 1, wherein the implantable medical device is configured to start generating and delivering the electrical stimulation signal in response to receiving the communication signal from the external device upon the external device being within a communication range of the implantable medical device.

9. The system of claim 1, wherein the rectifier comprises a rectifier coupled to the implantable antenna in parallel to the target device.

10. The system of claim 1, wherein the implantable antenna extends from the implantable medical device as a fixation member for stabilizing an implant position of the implantable medical device.

11. A method, comprising:
enabling an external medical device comprising an inductive communication initiating device and an external antenna to apply a communication signal to the external antenna;
receiving on an implantable antenna of an implantable medical device the communication signal inductively coupled between the external antenna and the implantable antenna, the implantable medical device comprising an inductive communication target device coupled to an implantable antenna, a control unit, a signal generator, a plurality of electrodes coupled to the signal generator, and a rectifier coupled to the implantable antenna;
generating a voltage output signal at a voltage output of the rectifier in response to the inductively coupled communication signal;
measuring, by a sampling circuit, a voltage signal correlated to one of the inductively coupled signal and the voltage output signal for providing the control unit with a feedback control signal;
providing the voltage output signal to the signal generator as a sole power source for powering generation of a therapeutic electrical stimulation signal delivered by the plurality of electrodes to a neurostimulation site of a patient; and
altering control of the signal generator based on the feedback control signal.

12. The method of claim 11, further comprising powering at least one of the implantable medical device control unit and the target device by providing the voltage output signal to the at least one of the control unit and the target device.

13. The method of claim 12, further comprising solely powering the functions of the implantable medical device from the voltage output signal.

14. The method of claim 11, further comprising generating the voltage output signal from a rectifier included in the target device.

15. The method of claim 11, further comprising coupling the voltage output signal to a rechargeable energy storage device included in the implantable medical device; and
recharging the energy storage device from the voltage output signal.

16. The method of claim 11, further comprising inductively coupling a communication carrier signal between the external antenna and the implantable antenna for generating the voltage output signal for a full duration of a neurostimulation therapy session.

17. The method of claim 16, further comprising:
modulating the carrier signal to encode communication data in the communication signal;
inductively coupling the communication signal comprising an interval of communication data during the therapy session; and
enabling the rectifier to generate the voltage output signal in response to the communication signal during the interval of communication data.

18. The method of claim 11, further comprising generating and delivering the electrical stimulation signal in response to receiving the communication signal from the external device upon the external device being within a communication range of the implantable medical device.

19. The method of claim 11, further comprising coupling the rectifier to the implantable antenna in parallel to the target device.

20. The method of claim 11, further comprising stabilizing an implant position of the implantable medical device using the implantable antenna extending from the implantable medical device as a fixation member.

21. An implantable medical device system, comprising:
an external device for transmitting a communication signal; and
an implantable device for receiving the communication signal by inductive coupling and configured to:
harvest power from the inductively coupled communication signal; and
power a signal generator from the harvested power to generate a therapeutic electrical stimulation signal;
the implantable device comprising a sealed housing enclosing electronic circuitry and an implantable antenna extending from the sealed housing, the implantable antenna having at least a portion electrically coupled to the electronic circuitry and having a bend in the portion of the implantable antenna for anchoring the implantable medical device at a target implant site of a patient,
the implantable antenna configured to receive the inductively coupled communication signal, wherein the power harvested from the inductively coupled communication signal comprises the sole source of power for the implantable device,
and wherein the implantable antenna is configured to be held in an undeployed position aligned with the sealed housing to allow the implantable device and the implantable antenna to be implanted through a skin incision.

22. The system of claim 21, wherein the implantable antenna comprises a dipole antenna.

23. The system of claim 21, wherein the implantable antenna comprises a magnetically-coupled loop antenna.

24. The system of claim 21, wherein the implantable antenna comprises a stent-like woven portion.

25. The system of claim 21, wherein the external device comprises a wearable external coupling device.

* * * * *

UNITED STATES PATENT AND TRADEMARK OFFICE
CERTIFICATE OF CORRECTION

| | | |
|---|---|---|
| PATENT NO. | : 9,585,642 B2 | Page 1 of 1 |
| APPLICATION NO. | : 14/098728 | |
| DATED | : March 7, 2017 | |
| INVENTOR(S) | : Dinsmoor et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 523 days.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*